United States Patent [19]

Dye et al.

[11] 3,976,278
[45] Aug. 24, 1976

[54] VALVE ASSEMBLY

[75] Inventors: John F. Dye; William J. Binard, both of Barrington; Bhupendra C. Patel, Elgin, all of Ill.

[73] Assignee: The Kendall Company, Boston, Mass.

[22] Filed: Jan. 8, 1975

[21] Appl. No.: 539,465

Related U.S. Application Data

[63] Continuation of Ser. No. 210,888, Dec. 22, 1971, abandoned.

[52] U.S. Cl............................ 251/149.6; 137/512.4; 137/512.5; 137/843; 137/606
[51] Int. Cl.².................... F16K 15/14; F16L 29/00
[58] Field of Search............. 137/608, 612.1, 512.5, 137/540, 606, 512.4, 525; 251/149.1, 149.4, 149.5, 149.6, 149.7; 128/221

[56] References Cited
UNITED STATES PATENTS

| | | | |
|---|---|---|---|
| 1,789,306 | 1/1931 | Ewald | 137/608 X |
| 1,958,155 | 5/1934 | Watkins | 137/512.5 |
| 2,138,988 | 12/1938 | Thomas | 137/512.5 X |
| 2,248,701 | 7/1941 | Fowler | 251/149.5 X |
| 2,256,656 | 9/1941 | Swabacker | 128/221 X |
| 2,268,020 | 12/1941 | Dahlstrom | 251/149.5 |
| 2,344,740 | 3/1944 | Shaff | 251/149.6 X |
| 2,372,408 | 3/1945 | Trich | 137/512.5 X |
| 2,383,249 | 9/1945 | Hardwick | 251/149.5 |
| 2,536,428 | 1/1951 | Dimitri et al. | 251/149.4 X |
| 2,564,977 | 8/1951 | Hu | 128/221 X |
| 2,582,546 | 1/1952 | Klein | 137/512.5 X |
| 3,093,134 | 6/1963 | Roehr | 128/221 |
| 3,189,046 | 6/1965 | Callahan et al. | 137/540 X |
| 3,192,949 | 7/1965 | De See | 137/540 |
| 3,218,025 | 11/1965 | Abelson et al. | 251/149.5 |
| 3,434,691 | 3/1969 | Hamilton | 128/221 X |
| 3,502,097 | 3/1970 | Muller | 137/612.1 X |
| 3,570,525 | 3/1971 | Borsom et al. | 251/350 X |
| 3,661,422 | 5/1972 | Sember et al. | 137/612.1 |

FOREIGN PATENTS OR APPLICATIONS

| 576,458 | 5/1924 | France | 251/149.4 |
|---|---|---|---|

*Primary Examiner*—William R. Cline
*Attorney, Agent, or Firm*—Powell L. Sprunger

[57] ABSTRACT

Apparatus for sampling and measuring the pressure of spinal fluid including, a valve, a spinal needle, a manometer and a receptacle. The valve includes a housing having an elongated chamber and a hollow stem extending outwardly from the housing and communicating with the chamber, and the needle is removably connected to the stem and communicates with the stem channel and the chamber. The valve has double-ended plug means biased against both ends of the chamber in sealing engagement to prevent the escape of fluid from the chamber. The manometer is removably connected to an end of the housing and has a hollow stem to retract one end of the plug means in the chamber to establish fluid communication between the chamber and manometer. The receptacle is removably attached to an end of the housing and has a hollow stem to retract one end of the plug means in the chamber to establish fluid communication between the chamber and the inside of the receptacle.

19 Claims, 11 Drawing Figures

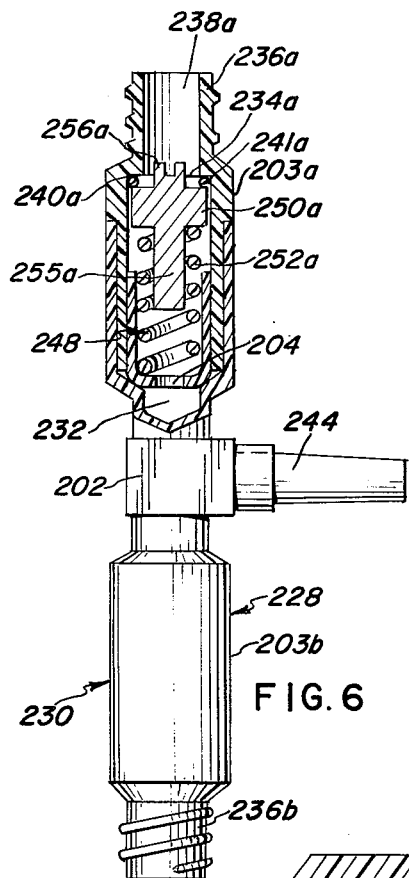
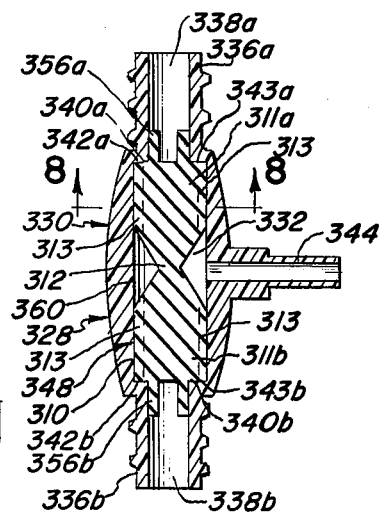
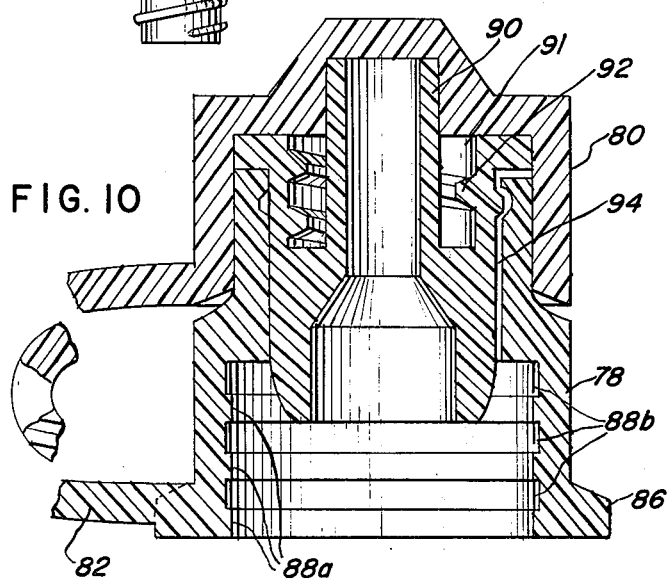
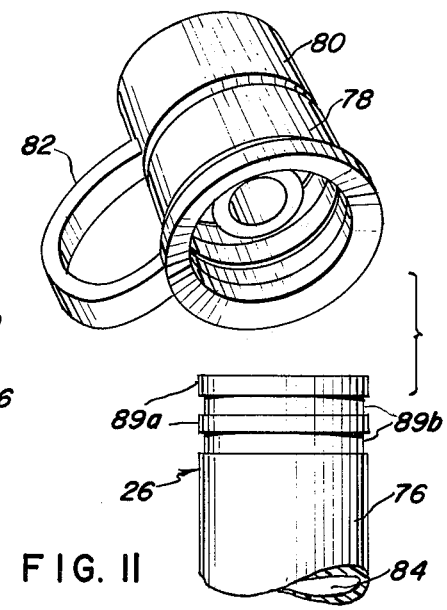
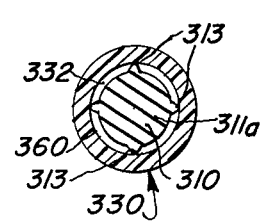

VALVE ASSEMBLY

This is a continuation, of application Ser. No. 210,888 filed Dec. 22, 1971, now abandoned.

BACKGROUND OF THE INVENTION

1. Field of the Invention

This invention relates to valves, and more particularly to a valve and apparatus for sampling and measuring the pressure of spinal fluid.

2. Description of the Prior Art

Instruments for measuring spinal fluid pressure are known, such as disclosed in Reiss et al U.S. Pat. No. 3,526,218, which shows a three-way stopcock for selectively taking fluid pressures and samples. However, such devices require a series of manipulations of the stopcock in order to measure the pressure and obtain samples, and have preassigned ports through which pressure measurements and samples are taken due to the required manipulations.

Also, in the prior art valves, a sample of spinal fluid is obtained by positioning a receptacle below the valve and allowing the fluid to drip or flow into the receptacle. Consequently, the fluid sample is exposed to the air while passing from the valve into the receptacle, and the sample may become contaminated during collection, which is undesirable, or may miss the receptacle and be lost.

In the past, after a pressure measurement has been taken, it has been necessary in such devices to retain a pressure measuring instrument, such as a manometer, on the device while fluid samples are being taken. However, this requirement is undesirable since the manometer causes inconvenience during completion of the sampling procedure due to its bulk and adds weight to a needle in the device which has been inserted into the spine.

Valves for catheter retention balloons are disclosed in Gould et al U.S. Pat No. 3,399,677, Harautuneian 3,385,301, Swanson U.S. Pat. No. 3,409,015, and Garth U.S. Pat. No. 3,087,492.

SUMMARY OF THE INVENTION

The principal feature of the present invention is the provision of apparatus for sampling and measuring the pressure of body fluids in a simplified manner.

The sampling and measuring apparatus of the present invention includes a valve, a hollow needle, a manometer and a fluid collection receptacle. The valve includes a housing having an elongated chamber and a pair of aligned nipples extending from opposite ends of the housing. Each of the nipples have a passageway communicating between the chamber and the outside of the housing. The housing also has a seat adjacent the inner end of each nipple relative to the chamber, and includes a stem extending outwardly from the housing intermediate the seats having a channel communicating between the chamber and the outside of the housing. The valve includes double-ended plug means which is biased in the chamber against both of the seats in sealing engagement. The needle is removably connected to the housing stem and communicates with the stem channel. Both the manometer and receptacle have a hollow stem which are receivable in the nipple passageways.

A feature of the invention is that the plug means prevents escape of fluid from the chamber when the manometer or receptacle is removed from the valve.

Another feature of the invention is that insertion of the manometer and receptacle stems into the nipple passageways retracts the plug means in the chamber to establish fluid communication between the chamber and the manometer and receptacle, respectively.

A further feature of the invention is the provision of means for releasably securing the manometer and receptacle to the housing nipples such that the associated ends of the plug means are sufficiently retracted in the chamber to establish fluid communication with the chamber.

Still another feature of the invention is that fluid communication is automatically established with the chamber when the manometer or receptacle is secured to the housing nipples.

Yet another feature of the invention is that the manometer and receptacle may be secured to either nipple of the housing.

Another feature of the invention is that the manometer and receptacle may be individually secured to the housing to separately measure and sample fluid.

A further feature of the invention is that the manometer and receptacle may be simultaneously secured to the housing nipples.

Still another feature of the invention is the provision of means for securing the manometer to the housing at a preselected position for pressure-indicating indicia on the manometer.

Further features will become more fully apparent in the following description of the embodiments of this invention and from the appended claims.

DESCRIPTION OF THE DRAWINGS

In the drawings:

FIG. 6 is an elevational view, taken partly in section of another embodiment of a valve for the apparatus of FIG. 1;

FIG. 7 is a sectional view of another embodiment of the valve for the apparatus of FIG. 1;

FIG. 8 is a sectional view taken substantially as indicated along the line 8—8 of FIG. 7;

FIG. 9 is a fragmentary sectional view of the manometer as partially secured to the valve of FIG. 7;

FIG. 10 is a fragmentary sectional view, on an enlarged scale, of a closure member and cap of the receptacle; and FIG. 11 is a fragmentary perspective view of the closure member and cap of FIG. 10 as removed from a vial of the receptacle.

DESCRIPTION OF THE PREFERRED EMBODIMENTS

Figure 1:
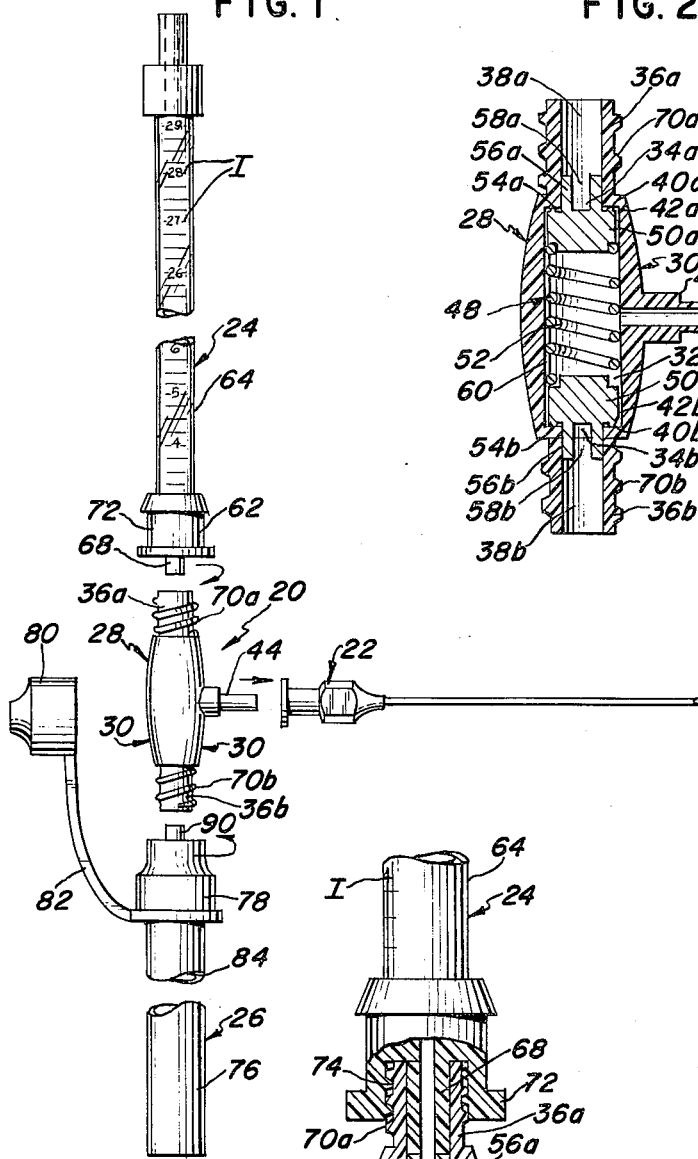
FIG. 1 is an exploded fragmentary elevational view of the sampling and measuring apparatus of the present invention.

Referring now to FIG. 1, a fluid sampling and pressure mesuring device designated generally 20 is shown including, a hollow needle designated generally 22, a manometer designated generally 24, a fluid collection receptacle designated generally 26, and a connecting valve designated generally 28. Although the device 20 is useful generally in obtaining samples and measuring the pressure of body fluids, it is particularly adapted in carrying out this function for a tap in the spinal column, and accordingly will be described further in this connection.

Figure 2:
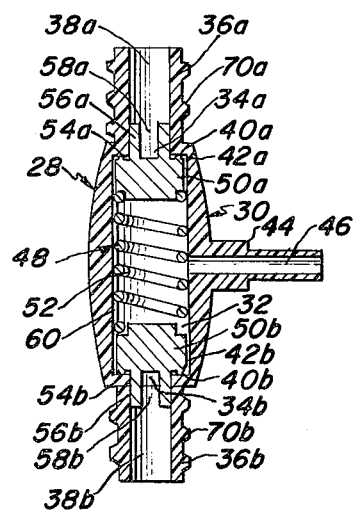
FIG. 2 is a sectional view of one embodiment of a valve for the apparatus of FIG. 1.

As illustrated in FIG. 2, the valve 28 includes a housing designated generally 30 having an elongated chamber 32, which preferably has a cylindrical shape, a pair of ports 34a and 34b at the ends of the chamber 32, and a pair of aligned nipples 36a and 36b extending from opposite ends of the housing 30. Each of the nipples 36a and b has a passageway 38a and 38b, respectively, which communicates between the chamber 32 and the outside of the housing 30. The housing 30 has a pair of seats 40a and 40b adjacent the ports 34a and b, respectively, which in this embodiment of the valve 28 comprises a pair of annular shoulders 42a and 42b in the chamber 32 extending peripherally around the associated port 34a and b, respectively. The housing 30 also has a stem 44 extending outwardly from the housing intermediate the ports 34a and b, and the stem 44 has a channel 46 extending through the stem and communicating between the chamber 32 and the outside of the housing 30.

The valve 28 has double-ended plug means designated generally 48 which is received in the chamber 32 and longitudinally biased against the seats 40a and b in sealing engagement to prevent escape of fluid from the chamber through the ports 34a and b. In this embodiment, the valve 28 includes a pair of plug elements 50a and 50b, slidably received in the chamber 32, and a helical spring 52 which urges the plug elements 50a and b against the seats 40a and b at opposite ends of the chamber. Each of the plug elements 50a and b has a ring 54a and 54b, respectively, integral with its outer end which serves as a sealing surface and engages the shoulder of the associated seats 40a and b, respectively. Each of the plug elements 50a and b has a finger 56a and 56b, respectively, at the end of the plug means 48 which extends into the passageway of the associated nipple 36a and b, respectively, and each of the fingers 56a and b has a transverse slot 58a and 58b at its end for a purpose which will be described below.

When force is applied through the nipple passageways to either of the plug elements 50a or b, the corresponding end of the plug means 48 retracts in the chamber away from the associated valve seat. Each of the plug elements 50a and b are slightly spaced from the wall 60 of the housing 30 which defines the chamber 32. Accordingly, when a plug element 50a or b retracts from the corresponding valve seat 40a or b, fluid communication is established between the corresponding passageway 38a or b and the chamber 32 around the sides of the corresponding plug element 50a or b, and since the stem channel 46 is in communication with the chamber 32, fluid communication is also established between the passageway and the channel 46. It is readily apparent that either of the plug elements 50a or b may be individually retracted into the chamber to establish fluid communication between the chamber and only one passageway, or both of the plug elements 50a and b may be simultaneously retracted into the chamber to establish fluid communication between the chamber and both of the passageways 38a and b. Further, the slots 58a and b in the corresponding fingers 56a and b permit fluid communication between the associated passageways 38a and b and the chamber 32 responsive to only a relatively slight retraction of the given plug element in the chamber.

Figure 3:
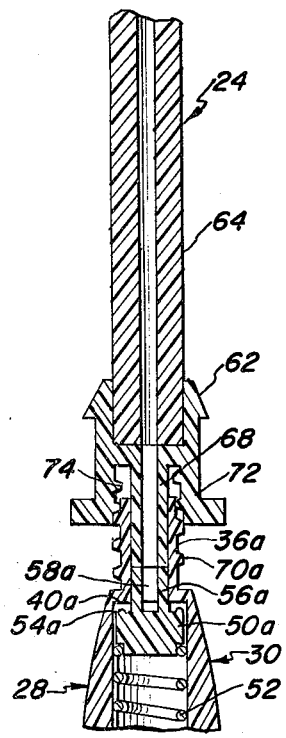
FIG. 3 is a fragmentary sectional view of a manometer of the apparatus of FIG. 1 as partially secured to the valve of FIG. 2.

As illustrated in FIG. 1, the manometer 24 has a lower base portion 62, a hollow gauge portion 64 extending from the base portion 62, to define a conventional open-ended manometer. However, it is understood that any suitable type of manometer may be utilized in the apparatus, such as a closed ended manometer. As shown in FIG. 3, the base portion 62 has a hollow depending stem 68 which is receivable in either of the nipple passageways 38a or b, and when the stem 68 is inserted into the passageway, the end of the stem engages the outer end of the associated plug element finger to retract the plug element in the chamber. Each of the nipples 36a and b has a thread 70a and 70b, respectively, on its outer surface, and the manometer base portion 62 has a depending annular flange 72 with a corresponding thread 74 to interengage with the nipple threads 70a or b. Thus, as the manometer is screwed onto either of the nipples 36a or b, , the manometer stem 68 engages the finger of the associated plug element, and retracts the plug element in the chamber to establish fluid communication between the chamber and the manometer. In the configuration as shown in FIG. 3, the manometer is partially screwed onto one of the nipples, and the plug element is partially retracted in the chamber, but sufficiently to establish fluid communication between the manometer and chamber through the finger slot.

Figure 4:
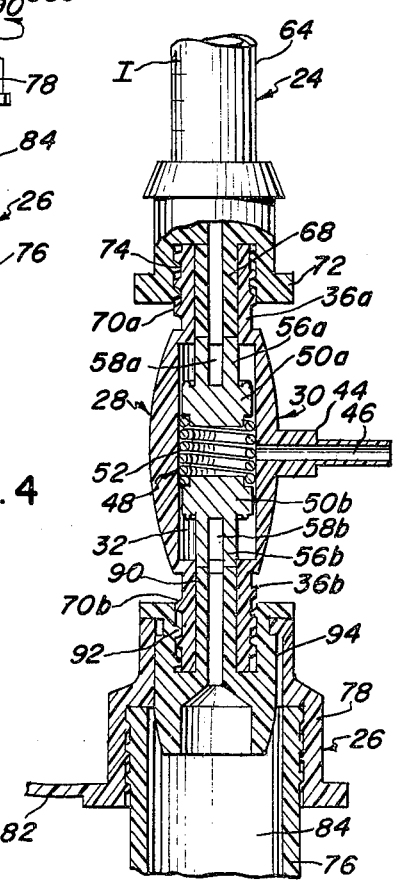
FIG. 4 is a fragmentary elevational view, taken partly in section, showing the manometer and a receptacle of the apparatus of FIG. 1 as secured to the valve of FIG. 2.

As illustrated in FIG. 1, the fluid collection receptable 26 has a vial 76, a closure member 78 removably secured to the vial 76, a cap 80 which may be removably secured to the closure member 78, and a strap 82 connecting the cap 80 and closure member 78. As shown in FIGS. 1 and 11 the vial 76 has a fluid retention cavity 84 which opens through the top of the vial. As illustrated in FIGS. 10 and 11, the closure member 78 includes a depending annular rim 86 having a plurality of alternating annular flanges and grooves 88a and 88b on its inner surface which interengage with a corresponding set of alternating flanges and grooves 89a and 89b at the top of the vial to removably secure the closure member in place and cover the top of the vial. As shown in FIG. 10, the closure member 78 has a hollow stem 90 which communicates between the vial cavity 84 and the outside of the closure member when the closure member is secured to the vial. Also, as shown in FIG. 4, the closure member 78 has a channel 94 extending through the closure member and communicating between the cavity 84 and the outside of the closure member to vent the vial during collection of fluid. As illustrated in FIG. 10, the closure member 78 also has an annular recess 91 extending around the stem 90, and a thread 92 on the surface of the recess 91 facing the stem 90. When the cap 90 is secured in place on the outer end of the closure member 78, the cap covers the outer end of the stem 90. Further details of the receptacle are disclosed in an application filed on Dec. 22, 1971, U.S. Pat. No. 3,811,592, by John F. Dye, one of the present applicants, and assigned to the same assignee.

When the cap 80 is removed from the closure member 78, the receptacle stem 90 may be received in either of the nipple passageways 38a or b, and the receptacle 26 may be screwed onto the associated nipple 36a or b, as shown in FIG. 4, with the thread 92 of the closure member 78 interengaging with the corresponding nipple thread 70a or b. As the closure member is screwed onto the nipple, the stem 90 engages the finger of the corresponding plug element 50a or b to retract the plug element in the chamber in a manner similar to that described in connection with the manometer. Thus, as the receptacle 26 is screwed onto the valve 28, fluid communication is established between the chamber 32 and the vial cavity 84 through the hollow stem 90.

In operation, the pointed end of the needle, along with a stylet (not shown), is inserted into the spinal column of the patient. After removal of the stylet from the needle, the valve 28 is removably secured to the needle by inserting the outer end of the housing stem 44 into the proximal end of the hollow needle, and fluid then flows from the spinal column through the needle and stem channel 46 into the chamber 32. The spinal fluid is confined in the chamber since both of the plug elements 50a and b are biased against the associated valve seats 40a and b. Preferably, during use of the apparatus 20, the nipple passageways 38a and b are generally aligned with the vertical due to the desirability of utilizing the manometer 24 and receptacle 26 in a vertical orientation, although, as previously notes, it is of no consequence as to which of the nipples is pointing up or down, since the manometer and receptacle can be secured to either end of the valve.

Next, either a pressure reading may be taken with the manometer or a sample may be obtained in the receptacle depending upon the preference of the user. If a pressure reading is first desired, the manometer 24 is screwed onto the upwardly directed nipple of the valve housing 30, as shown in FIG. 3, and fluid from the chamber 32 flows into the gauge portion 64 of the manometer providing a determination of the fluid pressure of the spinal column. Since the receptacle 26 is not yet attached to the valve 28, the lower end of the plug means 48 remains sealed while the pressure reading is being taken.

As shown in FIG. 4, when the manometer is fully secured to the housing nipple, indicia I, form which the amount of pressure is determined, faces in a direction opposed to that of the stem 44 and away from the patient's body when the apparatus is in use. Consequently, when the manometer is properly secured to the housing, the indicia I will always face in a direction which is convenient for taking a pressure reading. This result is accomplished by insuring that when the outer end of the housing nipple engages the base portion 62 of the manometer, at the fully secured position of the manometer, the indicia I is located at the preselected position. However, other suitable securing means between the manometer base portion and the housing nipples may be utilized to place the indicia I at the preselected position, such as a bayonet slot connection; pins in such a connection may be circumferentially misaligned to prevent the possibility of attaching the manometer to the housing in more than one position.

After the fluid pressure is determined, the manometer may then be removed from the housing 30, which automatically closes the uppper end of the valve, or the receptacle 26 may be secured to the lower end of the valve for a sample while the manometer is still in place on the valve. However, the reverse procedure of obtaining fluid pressure while the receptacle is in place on the valve is undesired, since fluid would flow into the receptacle and detract from the pressure measurement being taken in the manometer. Accordingly, when a determination of fluid pressure is desired, the manometer alone should be secured to the valve.

In order to obtain a fluid sample, the opened closure member is secured to the lower housing nipple. As discussed above, the closure member stem 90 automatically opens the valve 28 and establishes fluid communication between the housing chamber 32 and the receptacle cavity 84, and the cavity 84 is vented through the channel 94 to permit continuous passage of fluid into the receptacle while the receptacle 26 is secured in place on the valve. In the configuration as shown in FIG. 4, both the manometer and receptacle are secured to the valve, and a fluid sample would be obtained even though the manometer is also positioned on the valve.

When the desired amount of fluid is obtained in the receptacle, the receptacle is removed from the valve and the cap is secured to the outer end of the closure member 78 to cover the outer end of the hollow stem 90. Thus, with the cap secured to the closure member, the receptacle containing the fluid sample may be stored until it is needed for analysis. When it is desired to analyze the fluid sample, both the interengaged cap and closure member are removed from the top of the vial, as shown in FIG. 11, to provide access to the sample through the top of the vial, since it would be difficult to remove the sample through the stem 90 of the closure member without removing the closure member from the vial.

Figure 5:
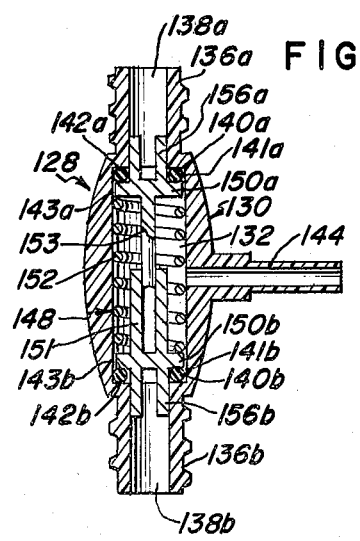
FIG. 5 is a sectional view of another embodiment of the valve for the apparatus of FIG. 1.

Another embodiment of the valve of the present invention is illustrated in FIG. 5, in which reference numerals are incremented by 100 to designate like parts. The housing 130 of the valve 128 which is similar in most respects to the housing of the valve of FIG. 2. However, in this embodiment, each of the valve seats 140a and b include an O-ring 141a and 141b, respectively, resting against the associated shoulder 142a and b, and the O-rings 141a and b sealingly engage against annular flat surfaces 143a and 143b, respectively, at the ends of the corresponding plug elements 150a and b. Also, one of the plug elements 150b includes a tube 151 extending toward the other plug element 150a in the chamber 132, and the other plug element 150a includes a pin 153 projecting toward the one plug element 150b, with the pin 153 being slidably received in the tube 151 to guide relative movement of the plug elements 150a and b in the chamber.

Another embodiment of the valve is illustrated in FIG. 6, in which the valve 228 includes a central portion 202 connected to the housing stem 244, and first and second end portions 203a and 203b extending from the central portion 202. Each of the first and second housing end portions 203a and b has a port, a seat, and a slidably received plug element, as previously described in connection with the valve of FIG. 2. As before, the chamber 232 extends longitudinally through the valve housing 230 between passageways of the nipples 236a and b and communicates in the central portion 202 with the hollow stem 244. The chamber 232 also extends through opening means 204 of the inner end of each of the housing end portions 203a and b. In this embodiment of the valve, each of the housing end portions 203a and b has a helical spring 252a and b (the latter of which is not shown) positioned intermediate the associated plug element 250a and b, respectively, and the central housing portion 202, and the springs bias the plug elements against the associated valve seat in sealing engagement, in a manner as previously described. Each of the plug elements 250a and b have a depending tongue 255a and 255b (the latter of which is not shown) received in the outer end of the associated springs to retain the plug elements and springs in place in the chamber.

Another embodiment of the valve of the present invention is illustrated in FIGS. 7–9, in which the valve 328 has a housing 330 which is similar to the housing 30 as described in connection with the valve 28 of FIG. 2. However, the plug means 348 is an integral compressible plug member 310 having a pair of end portions 311a and 311b and a central neck 312 of reduced diameter connected to the end portions 311a and b. Due to the resiliency of the plug member 310, annular sealing surfaces 343a and 343b on the outer ends of the end portions 311a and b are biased in sealing engagement against the annular shoulders 342a and b in the associated valve seats 340a and b. The plug member 310 has a pair of end fingers 356a and b received in the nipple passageways 338a and b, as previously described. As best illustrated in FIG. 8, both of the plug member end portions 311a and b are spaced from the housing wall 360 defining the chamber 332, and the plug member 310 has a plurality of longitudinally extending ribs 313 which are spaced peripherally around the end portions 311a and b and which engage the housing wall 360.

Thus, prior to attaching the manometer or receptacle to the valve 328, the plug means 348 sealingly engages against the valve seats to prevent passage of fluid between the nipple passageways and the chamber, as shown in FIG. 7. However, as illustrated in FIG. 9, as either the manometer or receptacle is attached to the valve, the plug member 310 compresses and retracts in the chamber to permit fluid communication between the chamber and the nipple passageways. As the plug compresses, fluid is permitted to pass around the end portions 311a and b of the plug member 310 between the longitudinally extending ribs 313.

The foregoing detailed description is given for clearness of understanding only, and no unnecessary limitations should be understood therefrom, as modifications will be obvious to those skilled in the art.

We claim:

1. A valve comprising, in combination;
a housing having an elongated cylindrical chamber, a port at each end of the chamber, a seat adjacent each of said ports and extending generally at right angles to the cylindrical wall of said chamber, a stem extending outwardly from the housing intermediate said seats and having a channel extending through the stem communicating between the chamber and the outside of the housing, and a pair of nipples extending from opposite ends of the housing, with each of said nipples having a passageway extending through the nipple and communicating with one of said ports;
double-ended plug means biased in the chamber against both of said seats in sealing engagement to prevent escape of fluid from the chamber through said ports, each end of the plug means individually retracting into the chamber away from the associated seat responsive to force applied to each end of the plug means to permit passage of fluid between the chamber and the associated ports, each end of the plug means having a generally cylindrical shape and being slightly spaced from the cylindrical housing wall, each end of the plug means having an annular shoulder associated with said seats, said shoulders extending generally at right angles from the outer cylindrical wall of said plug means;
a helical spring extending between the ends of the plug means to bias said shoulders toward said seats; and
annular O-ring means co-operating with said shoulders and said seats to provide sealing engagement between the plug means and seats when the shoulders of the plug means are biased by the spring toward the seats.

2. A valve assembly comprising, in combination:
a housing having an elongated chamber, a pair of aligned nipples extending from opposite ends of the housing, with each of said nipples having a passageway communicating between the chamber and the outside of the housing, a seat adjacent the inner end of each nipple relative to the chamber, and a stem extending outwardly from the housing intermediate the seats and having a channel communicating between the chamber and the outside of the housing;
double-ended plug means in longitudinally biased in the chamber against both of said seats in sealing engagement to prevent escape of fluid through said passageways, each end of the plug means individually retracting into the chamber away from the associated seat responsive to force applied to each end of the plug means to permit passage of fluid between the stem channel and associated nipple passageway;
fluid receiving means having hollow stem means receivable in the passageway of at least one of said nipples, said stem means having a sufficient length to contact and retract the associated end of the plug means;
means for removably securing the fluid receiving means to at least one of said nipples; and
a hollow needle communicating with said stem.

3. The valve of claim 2 including slot means co-operating between said stem means and plug means to permit fluid passage between the chamber and fluid receiving means.

4. The valve of claim 2 including sealing means co-operating between said stem means and associated nipple to prevent leakage of fluid.

5. The valve assembly of claim 2 wherein the securing means automatically locates the fluid receiving means at a predetermined angular relationship relative said housing.

6. A valve comprising, in combination:
a housing having an elongated chamber, a port at each end of the chamber, a seat adjacent each of said ports, and a stem extending outwardly from the housing intermediate said seats and having a channel extending through the stem communicating between the chamber and the outside of the housing;
double-ended plug means biased in the chamber against both of said seats in sealing engagement to prevent escape of fluid from the chamber through said ports, each end of the plug means individually retracting into the chamber away from the associated seat responsive to force applied to each end of the plug means to permit passage of fluid between the chamber and the associated port, said plug means comprising, a pair of plug elements slidably received in the chamber and means for urging the plug elements against opposite ends of the chamber, one of said plug elements including an integral tube extending toward the other plug element in the chamber, and the other plug element including an integral pin projecting toward the one plug element and slidably received in said tube to guide movement of the plug elements in the chamber; and a hollow needle communicating with said stem.

7. A valve comprising, in combination:

a housing having an elongated chamber, a port at each end of the chamber, a seat adjacent each of said ports, and a stem extending outwardly from the housing intermediate said seats and having a channel extending through the stem communicating between the chamber and the outside of the housing; and double-ended plug means biased in the chamber against both of said seats in sealing engagement to prevent escape of fluid from the chamber through said ports, each end of the plug means individually retracting into the chamber away from the associated seat responsive to force applied to each end of the plug means to permit passage of fluid between the chamber and the associated port, said plug means comprising a compressible plug member having a pair of end portions and a central neck of reduced diameter integrally connected to said end portions, said end portions being slidably retained in the chamber and having a sufficient length to prevent movement away from the walls of the chamber when the plug member is compressed.

8. The valve of claim 7 wherein the sides of said end portions are spaced slightly from the wall of the housing defining the chamber, and said plug member includes a plurality of longitudinally extending ribs spaced peripherally around said end portions and engaging the wall of the housing.

9. A valve assembly comprising, in combination:

a housing having an elongated chamber, a pair of aligned nipples extending from opposite ends of the housing, with each of said nipples having a passageway communicating between the chamber and the outside of the housing, a seat adjacent the inner end of each nipple relative to the chamber, and a stem extending outwardly from the housing intermediate the seats and having a channel communicating between the chamber and the outside of the housing;

double-ended plug means longitudinally biased in the chamber against both of said seats in sealing engagement to prevent escape of fluid through said passageways, each end of the plug means individually retracting into the chamber away from the associated seat responsive to force applied to each end of the plug means to permit passage of fluid between the stem channel and associated nipple passageway; and a hollow needle communicating with said stem.

10. The valve of claim 9 wherein each of said seats includes an annular shoulder in the chamber extending peripherally around the associated port, and each end of the plug means includes a sealing surface engagable against a seat.

11. The valve of claim 10 wherein each of said sealing surfaces comprise a ring integral with an end of the plug means and engagable against the shoulder in the associated seat.

12. The valve of claim 10 wherein each of said seats includes an O-ring intermediate the shoulder and associated end of the plug means.

13. The valve of claim 9 wherein said chamber has a cylindrical shape and the passageways in the nipples are generally aligned with each other.

14. The valve of claim 9 wherein each end of the plug means includes a finger extending into the passageway of the associated nipple, with each of the fingers having a transverse slot at its end to facilitate passage of fluid.

15. The valve of claim 9 wherein said plug means comprises a pair of plug elements slidably received in the chamber, and means for urging the plug elements against opposite ends of the chamber.

16. The valve of claim 15 wherein said urging means comprises a helical spring intermediate the plug elements.

17. The valve of claim 15 wherein the sides of said plug elements are slightly spaced from the wall of the housing defining the chamber to permit passage of fluid between the housing wall and plug elements.

18. The valve of claim 15 wherein said housing includes a central portion connected to the housing stem and first and second end portions extending from the central portion, with each of said first and second housing end portions having one of said ports, seats and slidably received plug elements, and wherein said urging means comprises a helical spring in each of said first and second portions intermediate the associated plug element and central housing portions.

19. The valve assembly of claim 9 wherein said needle is removably connected to said stem.

* * * * *